United States Patent [19]

Warren et al.

[11] 4,150,111

[45] Apr. 17, 1979

[54] ENTERIC COATED MAGNESIUM CHLORIDE

[76] Inventors: Allister Warren, 108 Lynnburn Rd., Lynnwood Manor, Pretoria; William H. Davis, 1119 Schoeman St., Hatfield, Pretoria, both of South Africa

[21] Appl. No.: 767,644

[22] Filed: Feb. 10, 1977

Related U.S. Application Data

[63] Continuation of Ser. No. 581,541, May 28, 1975, abandoned.

[30] Foreign Application Priority Data

May 28, 1974 [ZA] South Africa ............ 74/3391

[51] Int. Cl.$^2$ ............ A61K 33/06; A61K 9/36
[52] U.S. Cl. ............ 424/35; 424/153; 424/154
[58] Field of Search ............ 424/35, 153, 154

[56] References Cited

U.S. PATENT DOCUMENTS

| | | | |
|---|---|---|---|
| 1,716,686 | 6/1929 | Crossley | 424/154 |
| 1,830,313 | 11/1931 | Crossley | 424/154 |
| 1,845,486 | 2/1932 | Crossley | 424/154 |
| 2,589,900 | 3/1952 | Valmari | 424/154 |
| 3,081,233 | 3/1963 | Enz et al. | 424/35 X |
| 3,275,514 | 9/1966 | Saltman et al. | 424/154 |
| 3,371,015 | 2/1968 | Sjogren et al. | 424/35 X |
| 3,400,185 | 9/1968 | Kohnle et al. | 424/35 X |
| 3,420,931 | 1/1969 | Daum et al. | 424/35 X |
| 3,676,553 | 7/1972 | Reynolds | 424/153 X |
| 3,821,368 | 6/1974 | Reynolds | 424/154 X |

OTHER PUBLICATIONS

Nagera, Chem. Abstr. 24 #2804 (1930).
Craig, Chem. Abstr. 29 #843(9) (1935).
Barbour et al., Chem. Abstr. 22 #4639 (1928).
Sloan, Chem. Abstr. 21 #776 (1927).
Barbour et al., Chem. Abstr. 26 #523 (1932).
Moukhtar et al., Chem. Abstr. 21 #1845 (1927).

*Primary Examiner*—Shep K. Rose
*Attorney, Agent, or Firm*—Haseltine, Lake & Waters

[57] ABSTRACT

The invention provides for a tablet for the treatment of various human disorders and deficiencies comprising hexahydrate magnesium chloride contained in an enteric coating. In a preferred form of the invention the enteric coating is derived from a solution of cellulose acetate phthalate, castor oil, alcohol and acetone and overlies a sub-coating derived from a solution of polyvinylpyrolidone in alcohol.

6 Claims, No Drawings

ENTERIC COATED MAGNESIUM CHLORIDE

This is a continuation of application Ser. No. 581,541, filed May 28, 1975, now abandoned.

FIELD OF THE INVENTION

This invention relates to the administration of magnesium chloride in the treatment of various human disorders and deficiencies.

BACKGROUND TO THE INVENTION

The presence of magnesium in the human body is essential for the normal functioning of many enzyme reactions. It is the most important intra-cellular mineral after potassium and forms part of a multitude of actions with cellular enzymes. It also serves a number of functions in the human body such as in energy storing and releasing actions involved in oxidation phosphorylation. Indirectly, therefore, if affects all anabolic and catabolic reactions involving carbohydrate, fat and protein. It is an essential co-factor for some peptidases, ribonucleases, glycolic and cocarboxylation reations. A lack of magnesium chloride in the body can, therefore, give rise to a wide variety of disorders.

At the same time, magnesium chloride serves as a useful therapeutic agent in the treatment of a number of disorders, particularly disorders arising out of a magnesium imbalance. Such disorders include, for instance, idiopathic steatorrhea, resection of the bowel, ulcerative colitis and, in certain forms of chronic diarrhoea, rapid transition of food through the small intestine.

One of the difficulties encountered in the administration of magnesium chloride is that it is highly deliquescent. If exposed to the atmosphere, the powder is eventually dissolved in the moisture absorbed by it from the atmosphere. For this reason it is not practical to supply magnesium chloride in powder or tablet form.

Furthermore, magnesium chloride in both powder and tablet form is most unpalatable and can lead to nausea. Difficulty has been experienced in the past in coating the magnesium chloride in a palatable coating because moisture is still absorbed by it through the coating, leading to flocculation and eventual breakdown of the tablet.

The problem arising from the deliquescence of magnesium chloride cannot be overcome through administering it in solution form because not only is the solution unpalatable, leading to nausea, but magnesium chloride can be a stomach irritant causing retching and loss of the administered dosage.

Where there has been a sufficient intake of magnesium chloride for purposes of treatment, it has been found that as much as eighty per centum of the administered dosage can be excreted in the faeces. Generally, it is not possible, for this reason to administer sufficient magnesium chloride to obtain absorption of the chemical by the body in desired amounts.

An object of the present invention is the provision of magnesium chloride in a suitable dosage form in which the abovementioned problems are overcome to a large extent.

SUMMARY OF THE INVENTION

According to the invention there is provided a tablet including 150 to 350 milligrams magnesium chloride contained in an enteric coating.

Preferably, the magnesium chloride is provided in its hexahydrate form.

In one form of the invention, the enteric coating is derived from a solution of cellulose acetate phthalate, castor oil, alcohol and acetone.

Further according to the invention, a sub-coating is provided below the enteric coating, the sub-coating being derived from a solution of polyvinylpyrrolidone in alcohol.

The invention is also directed towards a method of treating human disorders including the steps of administering a tablet as set out above.

DESCRIPTION

By way of example only a preferred form of the invention will now be described.

A dry mixture of 13,375 kilograms hexahydrate magnesium chloride and 6,875 kilograms of calcium carbonate is made up and passed through a sieve. The dry mixture so obtained is then transferred to a champion mixer and one kilogram of lump-free polyvinylpyrolidone is added to the dry mixture. After mixing for ten minutes, one and one-half liters ethyl alcohol 95%, one and one-half liters acetone and 6 grams of an emulsifier and surface acting agent sold under the trade name Tween 80, are added to the dry mixture. Mixing is continued for ten minutes until the mixture is uniformly damp. At this stage the mixture has a crumb constituency and is sieved through a number eight sieve and placed on trays in a drying oven where it is dried at a temperature of 130° F. for twelve hours.

The granules so obtained are then passed through a number eighteen sieve. To these granules are added 300 grams of talc and 125 grams of magnesium stearate. Both the talc and the magnesium stearate act as lubricants.

The tablets are now formed on a 12 millimeter normal concave punch. These tablets are then sub-coated five times with a sub-coating solution comprising 30% polyvinylpyrolidone USP by weight made up in alcohol.

Thereafter the tablets are provided with an enteric coating derived from a solution made up as follows:
cellulose acetate phthalate—6%
castor oil—0,2%
alcohol absolute—35%
acetone—100% by weight.

After coating, the tablets are dried at 120° F. for six hours.

The tablets are now again sub-coated five times using the sub-coating solution referred to above, and rolled in talc before being dried at 120° F. for six hours.

Finally, the tablets are coated with a geranium rose solution to give them a pleasing appearance. The tablets are then dried in an oven at 120° F. for six hours and stored in sealed drums before being packed under humidity controlled conditions with silica gel sachets.

It has been found that in most instances a dosage of two to eight tablets per day provides relief. These may either be administered before retiring at night or at fixed intervals during the day, for instance, on awakening and on retiring to bed at night. In particular circumstances it may be necessary to administer a dosage above the level provided by eight tablets.

Magnesium chloride tablets manufactured according to the above process display the pharmacological properties of the magnesium ion when fully absorbed. The pharmacological properties of magnesium are threefold. It depresses nerve conduction, impairs vascular tone and cardiac function and accentuates the action of posterior pituitary hormones on the uterus. Laboratory scale experiments on human beings have indicated that it can be used with effect in the treatment of various forms of alcoholism, chronic liver diseases, porphyria, excessive lactation, hyperparathyroidism, serum calcium excess, malnutrition, pancreatitis, pregnancy at term, familial hereditary hypomagnesaemia, brain injuries, reactive hypoglycaemic tension and anxiety, manic and severe depressive states, insomnia and waking tiredness in conjunction with the use of diuretics, asthma, hypertension, primary or secondary aldosteronism, rheumatoid arthritis, joint pains, arthritis, hypokalaemia, chronic stress, diabetes mellitus, various forms of infertility, muscular fatigue, osteoporosis, mariestrumpels, etc.

The magnesium chloride tablet has the advantage over the fluid form of dosage in that it has a slower absorption rate thereby providing a more prolonged action and lessening the chances of loss through retching or in the faeces. Futhermore, the enteric coating ensures that the magnesium chloride passes through the stomach into the intestine, dispensing thereby with the chances of gastric irritation arising. By providing the magnesium chloride in tablet form, dosage units are more easily prescribed and intake is more readily controlled. At the same time, the difficulties arising out of the deliquescence of the magnesium chloride are largely overcome by the particular enteric layer described in the preferred embodiment.

We claim:

1. A tablet including 150 to 350 milligrams of magnesium chloride contained in an enteric coating.

2. A tablet as claimed in claim 1 in which the magnesium chloride is provided in its hexahydrate form.

3. A tablet including 300 to 700 milligrams of hexahydrate magnesium chloride contained in an enteric coating derived from a solution of cellulose acetate phthalate, caster oil, alcohol and acetone.

4. A tablet as claimed in claim 3 in which a sub-coating is provided beneath the enteric coating, the sub-coating being derived from a solution of polyvinylpyrrolidone in alcohol.

5. A method of treating magnesium-deficient patients which comprises administering to said patient a magnesium-replenishing effective amount of magnesium chloride contained in an enteric coating.

6. A method according to claim 5 wherein the magnesium chloride is in the hexahydrate form.

* * * * *